United States Patent [19]

Deutsch

[11] 4,433,058
[45] Feb. 21, 1984

[54] MEMBRANE RECEPTOR ASSAY
[75] Inventor: James W. Deutsch, New Haven, Conn.
[73] Assignee: The Regents of the University of California, Berkeley, Calif.
[21] Appl. No.: 237,210
[22] Filed: Feb. 23, 1981
[51] Int. Cl.$^3$ .................. G01N 33/60; G01T 1/00
[52] U.S. Cl. ........................ 436/504; 436/542; 436/804; 436/815
[58] Field of Search ................ 424/1, 12; 23/230 B; 436/504, 542, 804, 815

[56] References Cited

U.S. PATENT DOCUMENTS

| | | | |
|---|---|---|---|
| 4,033,722 | 7/1977 | Lindstrom | 23/230.3 |
| 4,078,049 | 3/1978 | Felix et al. | 424/1 |
| 4,202,875 | 5/1980 | Lindstrom | 424/1 |
| 4,239,745 | 12/1980 | Charm | 424/1 |

OTHER PUBLICATIONS

Raftery et al., Biochem. Biophys. Res. Comm. 45 (1971): 1622–1629.
Dunant et al., Chem. Abstracts, vol. 85, 1976 #30272n.
Schmidt et al., Anal. Biochem. 52 (1973) 349–354.
Stockley, J. Pharm. Pharmac., 1969, 21, 302–308.
Saelens et al., Arch. Int. Pharmacodyn., 186, 279–286 (1970).

*Primary Examiner*—Christine M. Nucker
*Attorney, Agent, or Firm*—Bertram I. Rowland

[57] ABSTRACT

Diagnostic assays are provided employing a naturally occurring membrane receptor for a compound of interest and a labeled antagonist and providing for competition between the antagonist and a sample suspected of containing the compound of interest. By measuring the partition of the labeled antagonist between the receptor and the liquid aqueous assay medium, the value can be related to the amount of compound of interest in the assay medium. Specifically, a membrane from electric ray organ is used as a source of acetylcholine receptor and labeled α-bungarotoxin is used as the antagonist. The assay medium containing the sample and α-bungarotoxin is combined with the water insoluble membrane, the membrane isolated, washed, and the amount of labeled α-bungarotoxin bound to the membrane determined. By employing samples having a known amount of acetylcholine, the measured signal can be related to the amount of acetylcholine in the sample.

5 Claims, No Drawings

MEMBRANE RECEPTOR ASSAY

BACKGROUND OF THE INVENTION

1. Field of the Invention

There is an ever increasing awareness of the relationship between the health of an individual and the proper balance of a large number of compounds which are naturally produced by the body or ingested. In the physiological study of the role specific compounds play in the regulation of physiological functions, it has become essential to determine small variations in concentrations of a variety of compounds. Therefore, there is an increasing desire to find ways to enhance the sensitivity and ease with which to measure a wide variety of compounds of physiological interest.

Most assays for compounds of physiological interest employ antibodies as one of the reagents. The preparation of antibodies useful in immunoassays for haptenic compounds involves preparing a conjugate of the hapten of interest with an antigen and injecting the antigen conjugate into a xenogeneic species. With highly functionalized haptens the synthesis of the conjugate can prove a serious obstacle. Even after preparation of the conjugate, there is no assurance that the antisera produced will have the desired specificity and binding constant to be useful in an immunoassay in the concentration range of interest.

2. Description of the Prior Art

McCaman and Stetzler (1977) J. Neurochem. 28, 669, describe an enzymatic assay for detecting acetylcholine. Spector et al., J. Neurochem. 30, 685 describe a radioimmunoassay for acetylcholine. Deutsch (1976), Ph.D. Thesis, Calif. Inst. of Technology, reports that acetylcholine affects the rate of binding of α-bungarotoxin to nicotinic acetylcholine receptor.

SUMMARY OF THE INVENTION

Novel competitive protein binding assays are provided involving the use of naturally occurring receptors for a compound of interest, particularly insolubilized in a membrane, and a labeled antagonist, which can complete with the compound of interest for the receptor site. By combining in an appropriate assay medium, the sample, the labeled antagonist, and the membrane-bound-receptor, and allowing the labeled antagonist to diffuse to the receptor in the assay medium, so as to be partitioned between the membrane and the liquid phase of the aqueous assay medium, the amount of bound or unbound labeled antagonist can be related to the amount of the compound of interest in the sample. Particularly, receptor for acetylcholine is used in conjunction with labeled α-bungarotoxin for the measurement of acetylcholine.

DESCRIPTION OF THE SPECIFIC EMBODIMENTS

Method and compositions are provided for performing assays for compounds for which naturally occurring receptors exist. The receptors which are employed are other than receptors formed to an immune response, such as antibodies. For the most part, the receptors will be receptors found in membranes having strong binding constants to a particular naturally occurring compound, where the receptors can be used in water insoluble form as part of the membrane, with the membrane either dispersed or bound to a support. Normally, the affinity of the receptor will be at least about $10^{-6}$, preferably $10^{-7}$, more preferably $10^{-8}$ M.

The reagent other than the receptor employed in the assay will be an antagonist to the compound of interest (analyte) which has been labeled. The antagonist will be capable of binding to the receptor in competition with the analyte, so that the partition of the labeled antagonist between the receptor and the liquid phase—bound or unbound—will be related to the amount of analyte in the assay medium. By antagonist is intended a compound having a different composition from the analyte with the affinity of the receptor for the antagonist being not more than a factor of 100 weaker, preferably at least equal, and frequently the affinity is a factor of 10 or more greater for the antagonist than for the analyte.

The receptors and analytes can be varied widely, depending upon the availability of a membrane receptor.

A number of different labels may be employed with the antagonist. The label must be chosen so as not to reduce the binding of the antagonist to the receptor below an acceptable level. Also, the label must allow for accurate detection to permit discrimination of the concentration of the analyte in the range of interest and with sufficient sensitivity to provide the desired degree of accuracy, depending upon whether a qualitative, semi-quantitative or quantitative result is desired.

A commonly used label is a radionuclide which may be used as an atom replacing another atom in a molecule. Illustrative of such atoms are $^3H$, $^{125}I$, $^{14}C$, $^{35}S$, and the like. Alternatively, the radionuclide may be part of a radical with $^{32}P$ as phosphate, $^{35}S$ as sulfate, and the like. Other labels which have also found use include stable free radicals, fluorescers, enzymes, magnetic particles, and the like. See, for example, U.S. Pat. Nos. 3,690,834, 3,791,932, 3,817,837, 3,996,345, whose disclosure to the extent they describe methods of preparation of labeled compounds and the manner in which assays can be carried out are incorporated herein by reference.

The source of the membrane will be cells having the desired receptor bound in the membrane. The receptor should have a high affinity for the ligand and antagonist, be stable during storage and under the conditions of the assay, and be relatively abundant.

In carrying out the assay, the membrane may be dispersed in the assay medium or fixed to a solid surface. It is found with the acetylcholine receptor that the receptor affinity is reduced when the membrane is bound to a solid surface. The solid surface may be part of a plate, tube, cuvette, particle, well or the like. The binding of the membrane to the surface may be as a result of adsorption, covalent bonding, non-covalent bonding, as in antigen-antibody binding, or any other method which allows for stable binding of the membrane to the surface during the various assay process steps.

Various surfaces may be involved, particularly organic surfaces, such as addition polymers, e.g. polyvinyl chloride, and the like. With many surfaces, it will be sufficient to add a dispersion of the membrane in buffer solution to the reaction vessel, where the membrane will then bind to the surface.

Where it is desirable to maintain the membrane dispersed in solution, the container should have an inert surface e.g. paraffin. Conveniently, a coated microtiter plate or cuvette can be used.

The assay medium will normally be an aqueous medium having from 0 to 40%, usually 0 to 20%, of an inert polar organic solvent. For the most part, the organic solvents will be ethers, amides, alcohols, or the like.

The assay medium will normally be buffered in the physiological range, usually from about 6 to 9, more usually from about 6.5 to 8, to provide for optimization of the assay sensitivity at the analyte level of interest. Various buffers may be used, with one buffer being preferred over another in a particular assay. Illustrative buffers include tris, phosphate, bicine, barbital, and the like. The concentration of buffer will generally be from about 1 to 50 mM, more usually about 1 to 10 mM, there being sufficient buffer to control the pH for the sample containing the analyte of interest. Another additive may be a small amount of protein, normally serum albumin, generally ranging in amount from about 0.5 to 2 weight percent. Other additives include salt, generally from about 50 to 200 mM to provide the appropriate ionic strength, stabilizers, biocides, esterase inhibitors e.g. neo-stigmine, or other additives which may play a specific role. The minor additives may range in concentration from about $10^{-6}$ to $10^{-2}$ M.

The sample may be obtained from a number of different sources, physiological or non-physiological. Where physiological, the source may be serum, urine, nerve or muscle biopsies, other organ biopsies, ocular lens solution, cerebrospinal fluid, or the like.

In performing the assay, the first step will be providing an assay medium having receptor bound membrane. Where the membrane is dispersed, this will involve adding the aqueous buffered dispersion of the membrane to a container having a non-adsorbent surface. Where the membrane is bound to a surface, this can be achieved in a number of ways, some of which have been indicated previously. In some instances, the membrane can be pre-prepared and bound covalently or non-covalently to a surface. Alternatively, a solution of the membrane may be added to the surface and the membrane allowed to adsorb to the surface.

To the membrane, either dispersed or bound, is then added the sample, normally as an aqueous buffered solution. The sample may or may not contain the labeled antagonist, depending upon whether simultaneous or sequential addition is desired. After the addition of the labeled antagonist, the reaction mixture is incubated at a mild temperature, normally from about 20° to 45° C., more usually from about 25° to 40° C. for a time sufficient to allow for a sufficient amount of the antagonist to diffuse to and bind to the membrane-bound-receptor. Generally, the time will be at least about 1 min and not exceed 6 hr, more usually from about 5 min to 3 hr. The time between the addition of the labeled antagonist and the measurement or first measurement, if there are a series of measurements, can be varied by varying the concentration of the antagonist, varying the dilution of the sample, varying the ionic strength, or the like. Where a rate determination is involved, usually there will be two or more measurements.

After a sufficient time for the binding to occur, the liquid assay medium is separated from the membrane. This can be achieved in a number of ways. In some instances, with the membrane fixed to a surface, decanting of the supernatant will be sufficient, followed by washings and combining the washings with the sample and the signal from the solution or the surface measured. With small volumes, the liquid may be absorbed with an appropriate absorbent paper, e.g., diethylaminoethyl paper. The paper may then be washed with buffered solution containing a small amount of nonionic detergent, generally from about 0.1 to 1%, more usually from about 0.05 to 0.3%. In this manner, unbound labeled antagonist is removed from the paper and may be measured. Alternatively, the antagonist bound to the membrane-bound-receptor bound to the paper may be measured. Where the membrane is bound to a surface e.g. vessel or particles, the vessel or particles may be measured. With a radionuclide, a scintillation cocktail may be prepared and the signal determined with a scintillation counter or a gamma counter may be employed.

With the other labels, the various techniques taught in the aforementioned patents may be employed. With a spin label, the sample may be introduced into an esr cavity and the electron spin resonance determined. With an enzyme, an enzyme assay can be performed. With a fluorescer, the sample may be irradiated with light in the absorption band and the fluorescence determined.

Where the membrane is measured, various techniques may be used, depending upon the label. The presence of the label may be measured either bound to the receptors in the membrane or the membrane digested to release the receptors or both the membrane and receptors digested to release the labeled antagonist. Enzymatic methods for digesting membranes and proteins are well known, as well as techniques for releasing compounds from their receptors. Either or both the soluble phase or the insoluble phase may be measured and the insoluble phase may be measured in insoluble or soluble form.

Depending on the nature of the competitive protein binding assay, a separation step may or may not be involved. A separation step is usually involved where the signal from the label cannot be readily distinguished between receptor bound and unbound labeled antagonist. In certain assays involving enzymes and fluorescers, the signal resulting from the label will vary significantly, depending upon whether the label is bound to receptor or unbound. Illustrative of these assays are the assays described in U.S. Pat. Nos. 3,817,837 and 3,998,943.

The significant factor in the assay is that binding of the label to the receptor allows for discrimination between label bound to receptor and unbound label in the liquid phase, either by allowing for separation between the liquid phase and the receptor-bound-label or by resulting in a substantially different signal between label in the liquid phase and label bound to receptor.

EXPERIMENTAL

The assays performed were for the determination of acetylcholine. The acetylcholine receptor employed was nicotinic acetylcholine receptor, although muscarinic receptor could be used, which is less preferable. The source of the membrane was from the electric ray organ. α-Bungarotoxin (αBuTX) was radioactively labeled with $^{125}I$. In carrying out the assay, 4 μl of receptor solution (1 nM αBuTX binding sites in 100 mM NaCl 5 mM tris-HCl, 1% bovine serum albumin, $10^{-4}$ M neo-stigmine, pH 7.4) is pipetted into the reaction vessel coated with Parafilm. To the receptor solution is added 2 μl of containing an unknown amount of acetylcholine in the above buffer, followed by four 4 μl of $^{125}I$-αBuTX (2 nM). After incubating the mixture for 1 hr at 37° C., the reaction is quenched by absorbing with diethylaminoethyl paper and the unbound α-BuTX is washed from the paper with a buffered solution containing 0.1% Triton X-100, a nonionic detergent. The paper containing the membrane may then be counted in a gamma counter.

Alternatively, the membranes may be adsorbed to polyvinyl chloride microtiter wells, although there is some reduction in affinity for the acetylcholine by the receptor. The assay is carried out in substantially the same way, except the assay medium is decanted, the membrane bound to the titer plate washed and the signal from the bound labeled α-BuTX determined.

In the presence of 5 nM acetylcholine, the binding of α-BuTX is reduced by 50%. Therefore, in a reaction volume of 10 ml, $5 \times 10^{-14}$ mole acetylcholine slows the reaction 50% and a reduction in rate of $1 \times 10^{-14}$ mole is detectible.

By employing naturally occurring antagonists, high binding constants can be achieved between the antagonist and the membrane receptor. In not requiring the analyte for preparation of labeled reagent, which analyte may be only difficultly available, a complex mixture, and/or difficult to label, an important alternative is provided by the subject invention. In this way, in many instances, a stable labeled compound can be prepared which effectively competes with the analyte of interest. By virtue of the use of the membranes, easy separation can generally be achieved between labeled antagonist bound to the receptor in the membrane and unlabeled antagonist. Many antagonists lend themselves to being labeled by a wide variety of labels which are presently used in other competitive protein binding assays.

Although the foregoing invention has been described in some detail by way of illustration and example for purposes of clarity of understanding, it will be obvious that certain changes and modifications may be practiced within the scope of the appended claims.

What is claimed is:

1. A method for determining in an aqueous assay medium the presence of acetylcholine in a sample suspected of containing said acetylcholine, said method employing a cell surface membrane receptor to said acetylcholine which is bound to said membrane and insoluble in said assay medium and a labeled antagonist to said acetylcholine, wherein said acetylcholine and said labeled antagonist specifically compete for the binding sites of said membrane-bound receptor and said label provides a detectable signal, the measured signal being related to the amount of label bound to receptor and unbound label;

said method comprising:
combining substantially simultaneously in an aqueous buffered medium said membrane-bound receptor, said sample and said labeled antagonist;
incubating for sufficient time to allow for competition between labeled antagonist and acetylcholine resulting in partitioning of said labeled antagonist between said membrane-bound receptor and said assay medium in proportion to the amount of acetylcholine in said medium; and
determining the level of signal as a result of said partitioning.

2. A method according to claim 1, wherein said label is a radionuclide and said determining involves separating labeled antagonist bound to receptor and unbound labeled antagonist.

3. A method according to claim 1, wherein said membrane is electric ray organ.

4. A method according to claim 3, wherein said medium is buffered to a pH in the range of about 6 to 9.

5. A method according to claim 1, including the additional step after said incubating step of absorbing said aqueous medium with an absorbent, freeing said absorbent of unbound labeled antagonist, and determining the signal from said label bound to said absorbent.

* * * * *